(12) United States Patent
Sah et al.

(10) Patent No.: US 6,913,925 B1
(45) Date of Patent: Jul. 5, 2005

(54) HUMAN MESENCEPHALON CELL LINES AND METHODS OF USE THEREFOR

(75) Inventors: Dinah W. Y. Sah, La Jolla, CA (US); Heather K. Raymon, La Jolla, CA (US)

(73) Assignee: Signal Pharmaceuticals LLC, San Diego, CA (US)

( * ) Notice: Subject to any disclaimer, the term of this patent is extended or adjusted under 35 U.S.C. 154(b) by 0 days.

(21) Appl. No.: 09/134,771

(22) Filed: Aug. 12, 1998

(51) Int. Cl.[7] .......................... C12N 5/08; C12N 5/00; C12N 15/00; C12N 15/63; C12P 21/06

(52) U.S. Cl. ................. 435/368; 435/69.1; 435/320.1; 435/325; 435/455; 435/363; 435/366; 435/375; 435/377; 435/383; 435/384

(58) Field of Search .......................... 435/69.1, 320.1, 435/325, 363, 366, 368, 375, 377, 383, 384, 455, 440, 365; 536/23.1

(56) References Cited

U.S. PATENT DOCUMENTS

| | | | | |
|---|---|---|---|---|
| 5,411,883 A | * | 5/1995 | Boss et al. ............... | 435/240.2 |
| 5,750,376 A | * | 5/1998 | Weiss et al. ............. | 435/69.52 |
| 6,197,585 B1 | | 3/2001 | Stringer ...................... | 435/440 |

FOREIGN PATENT DOCUMENTS

| | | |
|---|---|---|
| GB | 2 294 946 A | 5/1996 |
| WO | WO 91/09936 | 7/1991 |
| WO | WO 96/14398 | 5/1996 |
| WO | WO 96/14400 | 5/1996 |

OTHER PUBLICATIONS

Casper et al., EGF enhances the survival of dopamine neurons in rat embryonic mesencephalon primary cell culture, 1991, J Neurosci Res, vol. 30, pp. 372–381.*

Nikkhah et al., Platelet–derived growth factor promotes survival of rat and human mesencephalic dopaminergic neurons in culture, 1993, Experimental Brain Research, vol. 92, pp. 516–523.*

Hosimaru et al. PNAS. 93:1518–1523, 1996.*

Prasad et al. In Vitro. Cell Dev. 30A:596–603, 1994.*

Gallyas et al. Neurochem. Res. 22(5):569–575, 1997.*

U.S. Appl. No. 08/711,628, to Sah et al., filed Sep. 3, 1996, entitled: "Human CNS Cell Lines and Methods of Use Therefor" allowed Feb. 25, 2003.

di Porzio et al., "Establishment and Characterization of a Neuronal Cell Line, Obtained by c–myc Immortalization of Mouse Mesencephalic Cells," *Society for Neuroscience Abstracts* 18(1–2), p. P410, 1992.

Hartikka et al., "Cyclic AMP, but not Basic FGF, Increases the In Vitro Survival of Mesencephalic Dopaminergic Neurons and Protects Them from MPP–Induced Degeneration," *Journal of Neuroscience Research* 32:190–201, 1992.

Heller et al., "Glial–Derived Neurotrophic Factor (GDNF) Induced Morphological Differentiation of an Immortalized Monoclonal Hybrid Dopaminergic Cell Line of Mesencephalic Neruonal Origin," *Brain Research* 725:132–136, 1996.

Sah et al., "Bipotent Progenitor Cell Lines from the Human CNS," *Nature Biotechnology* 15(6): 574–580, 1997.

Zhou et al., "The Response of Human and Rat Fetal Ventral mesencephalon in Culture to the Brain–Derived Neurotrophic Factor Treatment," *Brain Research* 656:147–156, 1994.

* cited by examiner

*Primary Examiner*—Jeffrey Fredman
*Assistant Examiner*—Sumesh Kaushal

(57) ABSTRACT

Conditionally-immortalized human mesencephalon cell lines are provided. Such cell lines, which may be clonal, may be used to generate neurons, including dopaminergic neurons. The cell lines and/or differentiated cells may be used for the development of therapeutic agents to prevent and treat a variety of neurological diseases such as Parkinson's disease. The cell lines and/or differentiated cells may also be used in assays and for the general study of mesencephalon cell development and differentiation.

17 Claims, 4 Drawing Sheets

HUMAN MESENCEPHALON CELL LINES AND METHODS OF USE THEREFOR

TECHNICAL FIELD

The present invention relates generally to human mesencephalon cell lines. The invention is more particularly related to conditionally-immortalized mesencephalon cell lines capable of differentiation into dopaminergic neurons, and to differentiated cells derived from such cell lines. Such cell lines and/or differentiated cells may be used for development of therapeutic agents and for the treatment of diseases such as Parkinson's disease. The present invention is also related to the use of such cell lines and/or differentiated cells within various assays and for the study of mesencephalon development and differentiation.

BACKGROUND OF THE INVENTION

In the mammalian brain, dopamine systems are critical for the control of movement, hormone release, emotional balance and reward. Alteration of dopaminergic neurotransmission is involved in a variety of nervous system disorders. One such disorder is Parkinson's disease, which results from an intrastriatal deficiency in dopamine. Currently, there is no adequate method for treating or preventing the disease. L-DOPA has been administered to patients with Parkinson's disease, but such treatments are not generally considered to be effective.

Grafts of fetal neural tissue, such as mesencephalic tissue which contains dopaminergic neurons, have been shown to improve the symptoms of parkinsonism in humans and animal models. However, the use of such grafts has been limited, due in part to the difficulty in obtaining an adequate supply of transplant tissue. In addition, such tissue has not responded well to freezing, requiring the implantation of fresh tissue. In general, the use of fresh tissue is inconvenient and undesirable, since a period of time for evaluation of the tissue (e.g., to identify any viral contaminants) is beneficial.

Accordingly, there is a need in the art for stable mesencephalon cell lines that can be readily differentiated, and can be used as a renewable source of human mesencephalon dopaminergic neurons for Parkinson's research and drug discovery. The present invention fulfills these needs and further provides other related advantages.

SUMMARY OF THE INVENTION

Briefly stated, the present invention provides conditionally-immortalized human mesencephalon cell lines capable of differentiation into neurons. In one aspect, the present invention provides methods for producing a conditionally-immortalized human mesencephalon neural precursor cell, comprising the steps of: (a) transfecting human mesencephalon cells plated on a first surface and in a first growth medium that permit proliferation with DNA encoding a selectable marker and an externally regulatable growth-promoting gene; and (b) selecting the transfected cells on a second surface and in a second growth medium that permit attachment and proliferation, and therefrom producing a conditionally-immortalized human mesencephalon neural precursor cell. Within certain embodiments, the first and second surfaces are independently selected from the group consisting of substrates comprising one or more of a polyamino acid (e.g., polylysine or polyornithine), fibronectin, laminin or tissue culture plastic. The growth-promoting gene may be an oncogene, such as v-myc, and expression of the growth-promoting gene may, but need not, be inhibited by tetracycline.

Within other aspects, the present invention provides conditionally-immortalized human mesencephalon neural precursor cells capable of differentiation into dopaminergic neurons and conditionally-immortalized human mesencephalon neural precursor cells capable of differentiation into GABA-ergic neurons.

The present invention further provides methods for producing neurons, comprising culturing a conditionally-immortalized human mesencephalon neural precursor cell as described above under conditions inhibiting expression of the growth-promoting gene. Within certain embodiments, the cell may be cultured in medium comprising tetracycline and/or in the presence of one or more differentiating agents such as forskolin, GDNF, CNTF, IGF-I and/or BDNF.

Within further aspects, the present invention provides neurons produced as described above.

The present invention further provides, within other aspects, methods for transplanting a human mesencephalon cell into a mammal, comprising administering to a mammal a cell produced as described above.

Within further aspects, methods are provided for treating Parkinson's disease in a patient, comprising administering to a patient a cell produced as described above.

In other aspects, methods are provided for screening for an agent that modulates an activity of a protein produced by a human mesencephalon cell, comprising: (a) contacting a cell produced as described above with a candidate agent; and (b) subsequently measuring the ability of the candidate agent to modulate an activity of a protein produced by the cell.

Within further aspects, the present invention provides methods for detecting the presence or absence of a protein in a sample, comprising: (a) contacting a sample with a cell produced as described above; and (b) subsequently detecting a response in the cell, and therefrom detecting the presence of a protein in the sample.

The present invention further provides methods for identifying a human mesencephalon gene or protein, comprising detecting the presence of a gene or protein within a culture of cells produced as described above.

In further aspects, methods are provided for screening for an agent that affects human mesencephalon cell death, comprising: (a) contacting a cell produced as described above with a candidate agent under conditions that, in the absence of candidate agent, result in death of the cell; and (b) subsequently measuring the ability of the candidate agent to affect the death of the cell.

The present invention further provides methods for screening for a protein that regulates human mesencephalon cell death, comprising: (a) altering the level of expression of a protein within a cell produced as described above; and (b) subsequently measuring the effect of the alteration on the death of the cell, and therefrom identifying a protein that regulates human mesencephalon neural precursor cell death.

Within other aspects, the present invention provides conditionally-immortalized human mesencephalon neural precursor cells produced as described above. Such cells may be present within a clonal cell line.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1A shows the cells after growth in proliferative conditions. FIG. 1B shows the cells after 6 days of differentiation with DMEM/F12 medium containing N2 supplements, forskolin (10 µM), BDNF (20 ng/mL) and GDNF (20 ng/mL).

DETAILED DESCRIPTION OF THE INVENTION

Figure 1A:
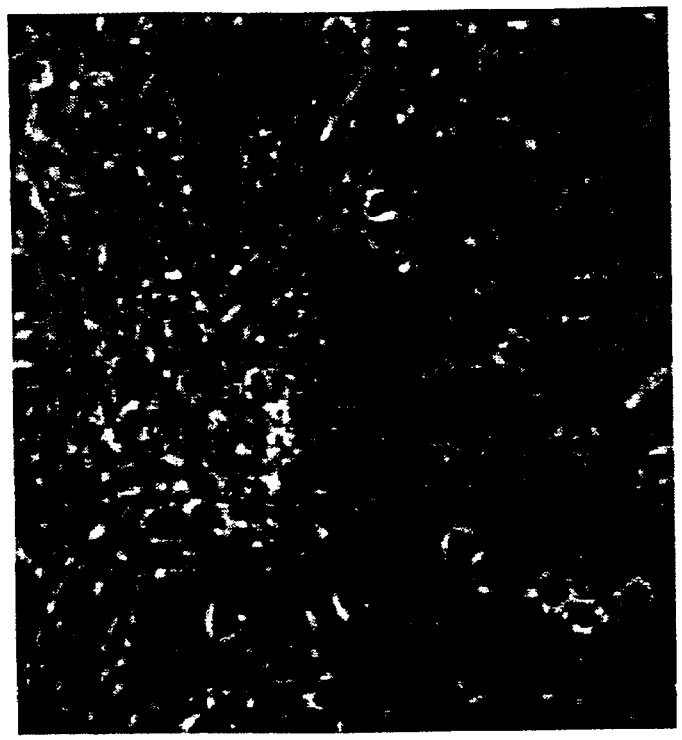
FIGS. 1A and 1B are phase contrast micrographs of immortalized human mesencephalon cells.

As noted above, the present invention is generally directed to conditionally-immortalized human mesencephalon cell lines, differentiated cells generated from such cell lines and various methods employing such cells. In particular, the present invention is directed to conditionally-immortalized human mesencephalon neural precursor cells that are capable of differentiation into dopaminergic neurons, and to the use of such cells for drug discovery and development, transplantation studies, therapeutic methods and a variety of assays. Conditionally-immortalized human mesencephalon neural precursor cell lines of the present invention may, but need not, be clonal cell lines. The cell lines described herein provide an infinite, renewable supply of homogeneous cells and facilitate treatment of, and drug development for, disorders such as Parkinson's disease.

Conditionally-immortalized human mesencephalon neural precursor cells may generally be prepared from human mesencephalon tissue (e.g., fetal mesencephalon tissue). Such tissue is preferably dissociated, using standard procedures. The tissue is then washed and plated on a surface and in a growth medium that permits proliferation (i.e., the surface and medium permit at least about 1% of the cells to double in a 24 hour period). One preferred growth medium contains DMEM/F-12, 10% fetal calf serum and FGF-2 (human recombinant, 40 ng/mL, Boehringer Mannheim, Indianapolis, Ind.). Suitable surfaces include, but are not limited to, one or a combination of polyamino acids (e.g., polylysire and/or polyornithine), tissue culture plastic and surfaces treated with laminin or fibronectin. Cells may generally be plated at a density ranging from $10^3$ to $10^5$ cells/cm$^2$, preferably at a density of approximately $3 \times 10^4$ cells/cm$^2$.

Human mesencephalon neural precursor cells may be conditionally immortalized by transfection of the plated cells with any suitable vector containing a growth-promoting gene (i.e., a gene encoding a protein that, under appropriate conditions, promotes growth of the transfected cell) such that the production and/or activity of the growth-promoting protein is regulatable by an external factor. In a preferred embodiment the growth-promoting gene is an oncogene such as, but not limited to, v-myc. Other oncogenes that may be used as growth promoting genes include N-myc, c-myc, p53, SV40 large T antigen, polyoma large T antigen, Ela adenovirus and E7 protein of human papillomavirus. In general, a "growth promoting gene" is any gene that, when employed within a tet-controlled expression system as described herein, results in the generation of cultures of neural precursor cells which can be differentiated into neurons.

External regulation of the growth-promoting protein may be achieved by placing the growth-promoting gene under the control of an externally-regulatable promoter (i.e., a promoter whose activity may be controlled by, for example, modifying the temperature of the transfected cells or the composition of the medium in contact with the cells). In general, regulation of expression of the growth-promoting gene should be relatively tight (i.e., expression of the growth-promoting gene should generally be undetectable by immunofluorescent techniques as described herein when the promoter is repressed. For example, a tetracycline (tet)-controlled gene expression system may be employed (see Gossen et al., Proc. Natl. Acad. Sci. USA 89:5547–5551, 1992; Hoshimaru et al., Proc. Natl. Acad. Sci. USA 93:1518–1523, 1996). In the absence of tet, a tet-controlled transactivator (tTA) within this vector strongly activates transcription from $ph_{CMV*-1}$, a minimal promoter from human cytomegalovirus fused to tet operator sequences. tTA is a fusion protein of the repressor (tetR) of the transposon-10-derived tet resistance operon of E. coli and the acidic domain of VP16 of herpes simplex virus. Low, non-toxic concentrations of tet (0.01–1.0 µg/mL) almost completely abolish transactivation by tTA (i.e., v-myc is no longer detectable using an immunofluorescence assay as provided herein).

In a preferred embodiment, the vector further contains a gene encoding a selectable marker (e.g., a protein that confers drug resistance). The bacterial neomycin resistance gene (neo$^R$) is one such marker that may be employed within the present invention. Cells carrying neo$^R$ may be selected by means known to those of ordinary skill in the art, such as the addition of 25–200 µg/mL G418 to the growth medium. It will be readily apparent that other markers may be employed, and appropriate selections may be readily performed by those of ordinary skill in the art.

Transfection may be achieved by any of a variety of means known to those of ordinary skill in the art including, but not limited to, retroviral infection. In general, plated cells may be transfected by infection with a suitable retrovirus (e.g., VSV-G pseudotyped LINX v-myc retrovirus, as described further below). The use of VSV-G pseudotyped retrovirus is preferred, in order to obtain higher stock concentrations of virus, to obtain stocks in the medium of choice (after centrifugation) and to increase the infectivity of human cells. Recently developed (nontraditional) VSV-G pseudotyped retroviral vectors may be especially useful for the infection of human cells, since the receptor for the VSV-glycoprotein is more abundant and less species-specific than the receptors for traditional amphotropic envelope proteins. Moreover, VSV-G pseudotyped viral particles have been reported to withstand ultracentrifugation, allowing concentration of virus and resuspension in growth medium compatible with neural progenitor cell growth (Burns et al., *Proc. Natl. Acad. Sci. USA* 90:8033–8037, 1993).

For example, a mesencephalon neural precursor cell culture prepared as described above may be infected within five days after plating by incubation for about 12–24 hours (e.g., overnight) with retrovirus in the presence of polybrene (4–8 µg/mL). Retrovirus may then be removed by washing with fresh growth medium. Transfected cells carrying a selectable marker may generally be selected on a surface and in a growth medium that permit attachment and proliferation. The ability of a surface to permit attachment may be determined using visual microscopic inspection. In general, at least about 20% of the cells should adhere to the surface. One preferred growth medium contains DMEM/F-12 with N2 supplement (GIBCO, Baltimore, Md.), conditioned medium from rat CNS progenitor cells (50%; prepared as described by Sah et al., *Nature Biotechnology* 15:574–580, 1997), FGF-2 (human recombinant, 40 ng/mL, Boehringer Mannheim, Indianapolis, Ind.), EGF (human recombinant, 40 ng/mL, GIBCO. Baltimore, Md.) and PDGFA/B (human recombinant platelet-derived growth factor, 20 ng/mL, Boehringer Mannheim, Indianapolis, Ind.). Suitable surfaces include, but are not limited to, one or a combination of a polyamino acid (e.g., polylysine and/or polyornithine), tissue culture plastic and surfaces treated with laminin or fibronectin, as described above, and should grow as an adherent monolayer.

Following transfection, cultures may be maintained in a simplified growth medium containing, for example, DMEM/F-12 with N2 supplement, FGF-2 (40 ng/mL), EGF (40 ng/mL) and PDGFA/B (20 ng/mL). Cultures approaching confluence may be passaged by trypsinization and split 1:5. Typically, one T75 flask near confluence may yield $10^7$ cells, and cultures may be passaged every 3 to 7 days. Cells may also be frozen in liquid nitrogen for long-term storage.

Clonal cell lines may be isolated from a conditionally-immortalized human mesencephalon neural precursor cell line prepared as described above. In general, such clonal cell lines may be isolated using standard techniques, such as by limit dilution or using cloning rings. and expanded. Clonal cell lines may generally be fed and passaged as described above. Genomic Southern blots may be performed to confirm clonality.

Conditionally-immortalized human mesencephalon neural precursor cell lines (which may, but need not, be clonal) may generally be induced to differentiate into neurons by inhibiting the expression of the growth-promoting gene (i.e., suppressing the production and/or activity of the growth-promoting protein). For example, if the gene encoding the growth-promoting protein is under the control of an externally-regulatable promoter, the conditions (e.g. temperature or composition of medium) may be modified to suppress transcription of the growth-promoting gene. For the tetracycline-controlled gene expression system discussed above, differentiation may be achieved by the addition of tetracycline to suppress transcription of the growth-promoting gene. In general, 1–5 µg/mL tetracycline for 48 hours is sufficient to begin neuronal morphological differentiation, and the number of differentiated neurons increases during subsequent days. Such differentiation may be performed, for example, by plating the cells on a suitable substrate (e.g., one or a combination of polyamino acid, fibronectin, laminin or tissue culture plastic) in a medium consisting of DMEM/F-12 with N2 supplement and tetracycline (1–5 µg/mL). It has been found, within the context of the present invention, that differentiation is enhanced by the addition of forskolin (10 µM), GDNF (glial cell-derived neurotrophic factor; 20 ng/mL), CNTF (ciliary neurotrophic factor; 20 ng/mL), IGF-I (insulin-like growth factor; 100 ng/mL) and BDNF (brain-derived neurotrophic factor; 20 ng/mL). Culture medium may then be refreshed (e.g., every 2–4 days).

Certain differentiated cells are dopaminergic neural cells (i.e., neural cells that express dopamine). Such cells may be identified based on the presence of tyrosine hydroxylase (TH), an enzyme that is involved in the synthesis of dopamine. In general, a cell that expresses TH at a level detectable using standard immunofluorescence techniques is considered dopaminergic. GABA-ergic differentiated cells may be similarly identified based on the detection of GABA via immunofluorescence.

Characterization of both progenitor and differentiated cell lines may generally be performed using techniques well known to those of ordinary skill in the art, including morphological analysis of cell type, immunocytochemistry and PCR (to identify cell typespecific markers and receptors and to confirm the presence of the growth-promoting gene) and electrophysiological analysis of voltage- and ligand-gated currents. Briefly, neuronal cells may be identified morphologically based on the presence of phase bright cell bodies and long, thin processes. As noted above, neuronal markers include TH, which is a marker for dopaminergic neurons, and GABA, which is a marker for GABA-ergic neurons. Map2ab may also be used as a pan-neuronal marker. The presence or absence of such markers may be readily determined using standard immunofluorescence techniques (employing, for example, commercially available primary antibodies and fluorescent reagents) and the levels of mRNA encoding such markers may be determined using PCR or hybridization techniques. Electrophysiological analyses familiar to those of ordinary skill in the art may be employed to evaluate the ability of the cells to fire action potentials and to express sodium, calcium and potassium currents, as well as ligand-gated currents (e.g., dopamine (DA), N-methyl-D-aspartate (NMDA), kainate (KA) and γ-amino-n-butyric acid (GABA)), thereby determining the levels of functional channels and receptors.

Human conditionally-immortalized mesencephalon neural precursor cells may generally be used to produce dopamine-producing neurons in vitro or in vivo. For in vivo use, conditionally-immortalized mesencephalon neural precursor cells may be implanted, such that the cells differentiate in vivo. Alternatively, differentiated dopaminergic neurons generated in vitro may be implanted.

Implantation may generally be performed using any suitable technique known in the art. For example, cells may be inserted into a delivery device (such as a syringe) that facilitates introduction (by, for example, injection) of the cells to a desired location. Cells are generally present within a pharmaceutical composition as described herein for implantation.

Cells can generally be assessed for their ability to treat Parkinson's disease using any of a variety of animal models of the disease. Suitable rat models include rats having lesions in substantia nigral dopaminergic cells caused by treatment with 6-hydroxydopamine. 1 methyl-4-phnyl-1,2,3,6-tetrahydropyridine (MPTP) or by surgical transection of the nigral striatal pathway (see, e.g., Bjorklund et al., *Nature* 298:652–654, 1982). A rhesus monkey or sheep model may also be used, in which the animals have lesions in substantia nigral dopaminergic cells caused by treatment with MPTP (see, e.g., Smith et al., *Neuroscience* 52:7–16, 1993; Bakay et al., *Appl. Neurophysiol* 48:358–361; Zamir et al., *Brain Res.* 322:356–360, 1984; and Baskin et al., *Life Sci.* 54:471–479, 1994). Cells may be implanted using standard techniques and morphological and immunohistochemical studies can be performed to determine whether the implant has integrated into the surrounding tissue. Behavioral tests, such as the rotational symmetry model (Freed et al., in Sladek et al. (eds.) Neural Transplants: Development and Function (Plenum Press, NY):373–406, 1984), may be used to confirm functional integration.

For treatment of a patient, conditionally-immortalized human mesencephalon neural precursor cell lines and/or modulating agents (e.g., which may inhibit or enhance an activity of a protein produced by a human mesencephalon neural precursor cell, or may inhibit the death of differentiated human mesencephalon neural precursor cells, as described below) may be administered to a patient (either prophylactically or for treatment of an existing condition). Conditions that may be prevented and/or treated using such cells and/or modulating agents include, but are not limited to, Parkinson's disease. In particular, for treatment of Parkinson's disease, differentiated dopaminergic neural cells may be transplanted into, for example, the striatum of a patient. Cells may generally be introduced into the patient by grafting, using standard techniques. Modulating agents may be administered by any of a variety of routes known to those of ordinary skill in the art. Such agents may be administered in their active form, as prodrugs (i.e., compounds that are converted to the active form within the patient) or as nucleic acid sequences encoding the modulating agent or prodrug. Conditionally-immortalized human mesencephalon neural precursor cells for use in this aspect of the present invention may, but need not, be further transfected such that they express one or more additional proteins (such as modulating agents) within the patient.

For administration to a patient, one or more conditionally-immortalized human mesencephalon neural precursor cells (and/or modulating agents) are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. The selection of a carrier will depend, in part, on the nature of the substance (i.e., cells or chemical compounds) being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Routes and frequency of administration, as well as doses, will vary from patient to patient and with the nature of the substance being administered. In general, the pharmaceutical compositions comprising modulating agents may be administered intravenously, intramuscularly, subcutaneously or intracavity. Doses may be administered daily. Compositions comprising cells are generally implanted one or more times. A suitable dose is an amount that is sufficient to show improvement in the symptoms of a patient afflicted with a neurological condition such as Parkinson's disease or to inhibit the onset of such a condition. Symptom improvement may be detected based on improvement and/or delay in clinical symptoms associated with the disease. Symptom improvement may, but need not, occur weeks or months after administration or implantation. In general, the amount of modulating agent present in a dose, or produced in situ by DNA present in a dose, ranges from about 1 mg to about 200 mg per kg of host. Suitable dose sizes will vary with the size of the patient, but will typically range from about 0.1 mL to about 5 mL for 10–60 kg animal.

Within certain aspects of the present invention, conditionally-immortalized human mesencephalon neural precursor cell lines may be used in a variety of in vitro assays and screens. It will be apparent that the cell lines described herein may be used within numerous well known assays and screens, and that specific parameters and criteria for performing these methods will depend upon the assay being performed. Those of ordinary skill in the art can readily design specific assays and screens based upon well known methods and upon the desired properties of the compounds to be identified.

Within certain assays, the differentiated or undifferentiated conditionally-immortalized human mesencephalon neural precursor cell lines described herein may be used to detect the presence or absence of a nucleic acid molecule or protein of interest in such cells. To detect a particular nucleic acid sequence (i.e., DNA and/or RNA) within such cells, the well known methods of PCR and/or various hybridization techniques may be employed.

Such assays may be readily designed and performed using methods described, for example, in Sambrook et al., *Molecular Cloning: A Laboratory Manual*, Cold Spring Harbor Laboratories, Cold Spring Harbor, N.Y., 1989. To detect a protein, the detection reagent is typically an antibody, which may be prepared as described below. There are a variety of assay formats known to those of ordinary skill in the art for using an antibody to detect a protein in a sample. See, e.g. Harlow and Lane, *Antibodies: A Laboratory Manual*, Cold Spring Harbor Laboratory, 1988. Antibodies for use in such assays may be polyclonal or monoclonal. Antibodies may be prepared by any of a variety of techniques known to those of ordinary skill in the art and monoclonal antibodies specific for a protein of interest may be prepared, for example, using the technique of Kohler and Milstein, *Eur. J. Immunol.* 6:511–519, 1976, and improvements thereto. Alternatively, a protein may be detected based upon its activity, using any suitable assay known in the art.

Such assays may generally be used, for example, within methods to evaluate the ability of an agent to modulate an activity of a protein produced by a human mesencephalon neural precursor cell or a neuron. Within such assays, differentiated or undifferentiated cells may be contacted with a candidate agent under conditions and for a time sufficient to permit an agent to modulate protein activity. Following contact, the ability of the candidate agent to modulate an activity of a protein produced by the cell is measured using standard techniques, such as PCR or hybridization (for evaluating levels of mRNA) or any of a variety of immunoassays or functional assays appropriate for the protein of interest. For example, calcium-sensitive or voltage-sensitive dye coupled assays, cAMP measurements and/or receptor binding assays may be employed to evaluate the effect of a candidate modulating agent. In general, a suitable amount of antibody or other agent for use in such a screen will vary depending on the particular protein, but will range from about 10 $\mu$g to about 100 mg.

The term "modulation," as used herein, includes the suppression or enhancement of an activity of a protein of interest. Such modulation may occur at the transcriptional or translational level, or may be the result of altering the activity of the intact protein. Modulation of protein activity may be direct (i.e., the modulating agent may interact directly with the protein of interest) or may be indirect (i.e., the modulating agent may alter the expression and/or activity of one or more other proteins which in turn modulate the activity of the protein of interest). Modulating agents may be antibodies (e.g., monoclonal), polynucleotides or other drugs. Agents that modulate the activity of any cellular protein may be identified within such screens. In certain embodiments, modulating agents may be identified for proteins such as neurotransmitter receptors (e.g., DA-receptors, AMPApreferring receptors, kainate receptors, GABA receptors, adenosine receptors and/or 5-HT receptors), growth factor receptors (e.g., receptors for FGF-2, EGF, BDNF, NGF, CNTF, NT-3 and/or GDNF) or ion channels (e.g., sodium channels, calcium channels and/or potassium channels). Preferred modulating agents are able to suppress or enhance the activity of a protein by at least a factor of 2.

In another aspect of the present invention, the cell lines described herein may be used within a system for studying protein and/or gene expression in a native neural precursor or neuronal cellular environment. For example, receptor expression and/or activity may be assayed. and the effect of various modifications on such expression and/or activity may be evaluated using methods well known to those of ordinary skill in the art. In one such method, cell lines may be permanently or transiently transfected with one or more genes of interest such as, but not limited to, genes that produce or modify membrane proteins, secreted proteins or intracellular proteins of interest. Such genes include ion channels, neurotransmitter receptors, proteins mutated in familial forms of neurodegenerative diseases (e.g., synuclein) and/or MAP kinases. The transfected genes may also be coupled to reporter genes for use in drug development. Within this and other aspects described herein, conditionally-immortalized human mesencephalon neural precursor cells may be employed without differentiation, or differentiated cells may be used. In addition, cells of varying ages and grown in any of a variety of conditions may be employed. The cell lines of the present invention have many advantages over existing cell lines for such studies, including the ability to provide clonal cell lines capable of producing neurons, and the property of conditional-immortalization. which allows arrest at specific stages of development. The selection of particular cells for any given study will depend on the goals of the study, and those of ordinary skill in the art will be readily able to prepare appropriate cells using the techniques described herein.

Within further aspects, conditionally-immortalized human mesencephalon neural precursor cell lines or the present invention may be used in assays to detect the presence or absence of a particular protein in a sample. In general, an assay may be performed by contacting such cells with a sample and then measuring a response induced by the protein within the cells using methods familiar to those of ordinary skill in the art. For example, a response may be measured using differential display techniques.

In a further aspect, the conditionally-immortalized human mesencephalon neural precursor cell lines described herein may be used in the identification of novel genes and proteins present in proliferative and differentiated (e.g., dopaminergic neuronal) human mesencephalon neural precursor cells. Techniques, such as PCR, differential display, hybridization, expression library screens, immunoassays and two-hybrid screens may be employed for such identification. A particularly useful technique is differential gene screening. Clonal cell lines as described herein are particularly suited to such studies because they are derived from a single parental cell and, therefore, human mesencephalon neural precursor cell-specific genes are amplified with respect to non-clonal cell lines. Novel genes and proteins that are expressed upon experimental manipulation (e.g., induction of apoptosis) may also be identified.

The cell lines provided herein may also be used in in vitro models of neuronal cell death including, but not limited to, neuronal apoptosis induced by growth factor withdrawal. Briefly, a clonal conditionally-immortalized human mesencephalon neural precursor cell line may be differentiated under conditions designed to minimize the basal level of apoptosis. Suitable conditions may be readily identified by evaluating the percentage of apoptotic nuclei in cells grown under different test conditions. The percentage of apoptotic nuclei may generally be determined by methods well known to those of ordinary skill in the art, such as by DAPI staining or the in situ nick end-labeling assay. Suitable conditions for minimizing basal apoptosis include differentiation in the presence of 1 $\mu$g/mL tetracycline, forskolin (10 $\mu$M), IGF-I (100 ng/mL), CNTF (20 ng/mL). GDNF (20 ng/mL) and BDNF (20 ng/mL). Cells should be maintained in suitable differentiation conditions for a time sufficient to allow differentiation. while minimizing the basal level of apoptosis (which generally increases during the first 10 days of differentiation).

Such differentiated neuronal cells may then be employed in any of several models of apoptosis. In one such model, growth factors and N2 supplement are withdrawn for an amount of time sufficient to significantly increase the percentage of apoptotic cells with condensed nuclei. Preferably, the percentage of such apoptotic cells increases by at least about two fold. Under the representative conditions described above, about 18 hours of withdrawal is generally sufficient. After 48 hours of withdrawal, a significant percentage of the cells should be rendered nonviable. Preferably, at least about 50% of the neurons are no longer viable following withdrawal of growth factors.

Regardless of the particular model, the cells may be used to study the mechanisms of apoptosis, as well as the effect of various conditions and agents on the apoptosis of neuronal cells, using experimental techniques well known to those of ordinary skill in the art. For example, the cells may be used to screen for an agent that affects neuronal cell death. Such a screen may be performed by contacting the cells during growth factor withdrawal with a candidate agent and then evaluating the ability of the candidate agent to affect the subsequent level of apoptosis. Similarly, the cells may be used to screen for a protein that regulates neuronal cell death. In such a screen, the level of expression or activity of a candidate protein (e.g. an enzyme) is altered within the cells (using standard techniques) and then the affect of the alteration on the level of apoptosis following treatments (including, but not limited to, growth factor withdrawal) is measured.

The following Example is offered by way of illustration and not by way of limitation.

EXAMPLE

Preparation of Human Mesencephalon Progenitor Cell Lines

This Example illustrates the conditional immortalization of human mesencephalon progenitor cells.

Human mesencephalon cells in primary culture were prepared from first trimester human fetal brain (obtained through Advanced Bioscience Resources, Inc.). The tissue was procured in compliance with state and federal laws and regulations. The mesencephalon was dissociated by incubation at 37° C. for 30 to 45 minutes in an enzyme solution containing protease 23 (3 mg/mL), with occasional trituration. The dispersed mesencephalon cells were washed with saline containing trypsin inhibitor (1 mg/mL) and bovine serum albumin (1 mg/mL). The cells were subsequently plated at a density of approximately $3 \times 10^4$ cells/cm$^2$ in growth medium consisting of DMEM/F-12, 10% fetal calf serum and FGF-2 (human recombinant, 40 ng/mL. Boehringer Mannheim, Indianapolis, Ind.).

For retroviral infection, the LINX v-myc vector was employed (Hoshimaru et al., *Proc. Natl. Acad Sci. USA*, 93:1518–1523, 1996; Sah et al., *Nature Biotechnol.* 15:574–580, 1997). In this system, in the absence of tetracycline, a tetracycline-controlled transactivator (tTA) strongly activates transcription from $ph_{CMV*-1}$, resulting in the expression of the downstream v-myc oncogene. Tetracycline (0.01–1.0 µg/mL) almost completely abolishes transcriptional activation by tTA, thereby blocking transcription of the v-myc oncogene. A gene conferring neomycin resistance is also present in the vector. Mesencephalon cultures were retrovirally infected and G418-selected using methods analogous to those described by Sah et al., *Nature Biotechnol.* 15:574–580, 1997.

After G418 selection, cultures were maintained in a simplified growth medium consisting of DMEM/F-12 with N2 supplement, FGF-2 (40 ng/mL), EGF (40 ng/mL) and PDGF A/B (20 ng/mL). Cultures approaching confluence were passaged by trypsinization and split 1:5. Typically, one T75 flask near confluence yielded $10^7$ cells, and cultures were passaged every 3 to 7 days.

During G418 selection, some cell death occurred; after the selection, v-myc$^+$ cells became the predominant cell type in the culture. These G418-resistant, v-myc$^+$ cells grew as an adherent monolayer. The majority of the cells were polygonal with very short processes.

Figure 1B:
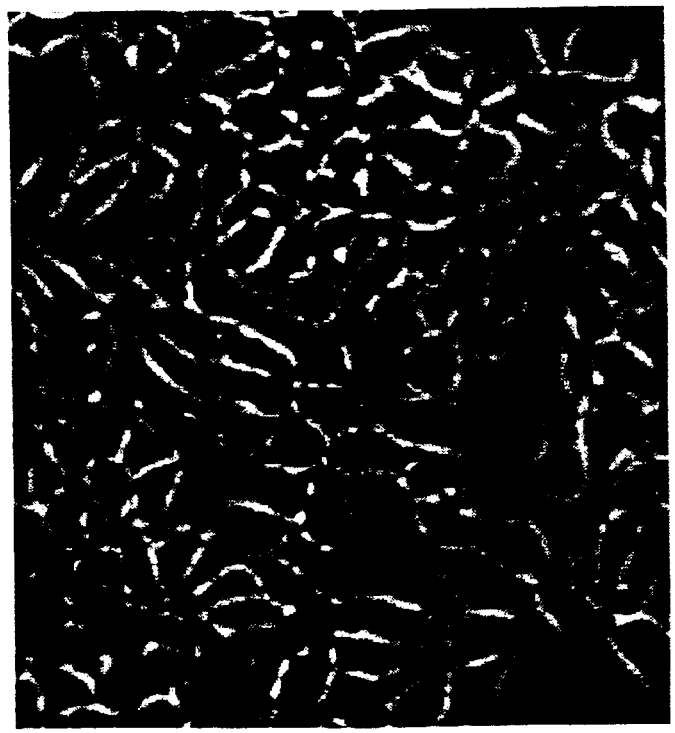
Figures 2A, 2B, 2C, 2D:
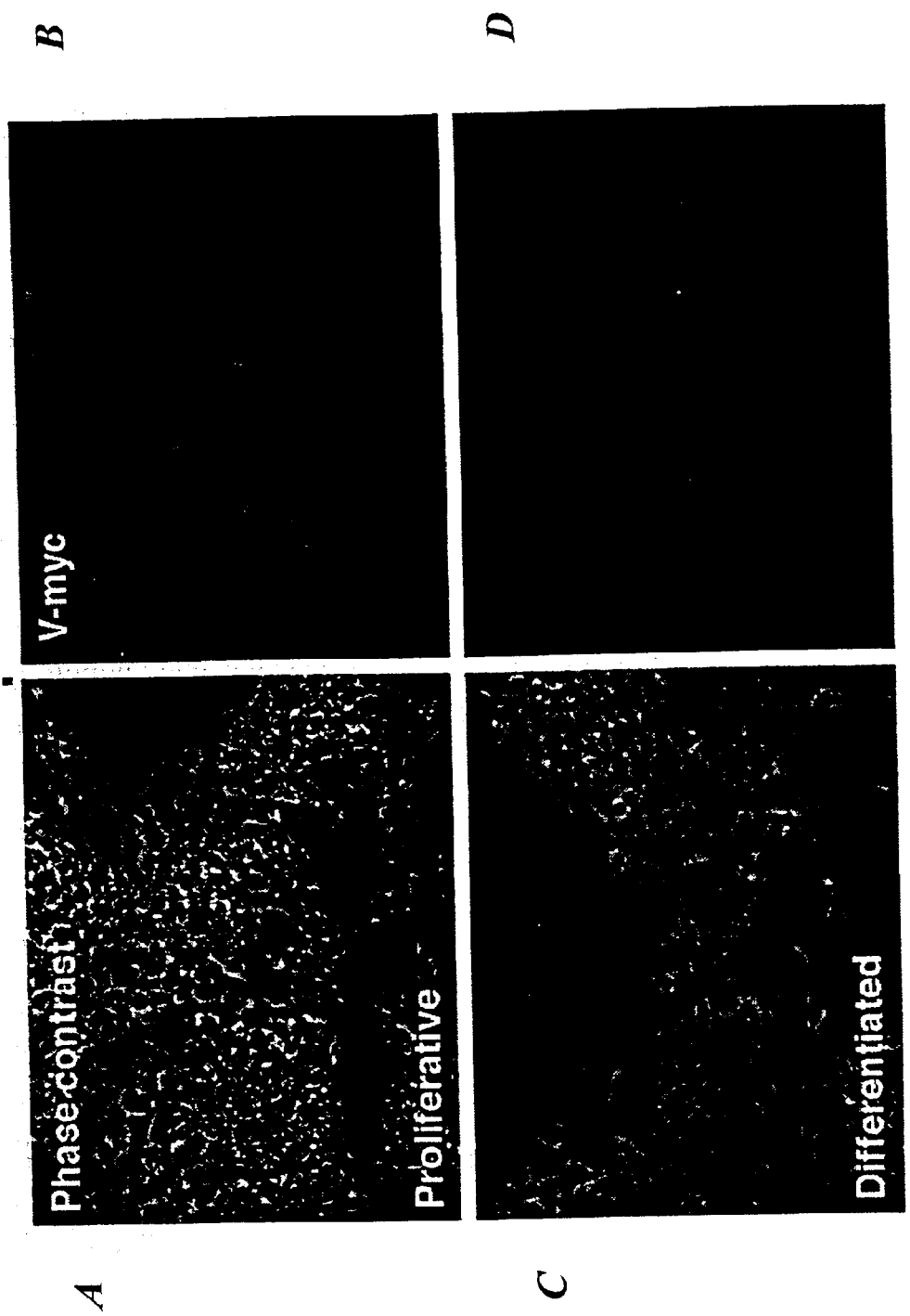
FIGS. 2A–2D are phase contrast micrographs (FIGS. 2A and 2C) and photographs (FIGS. 2B and 2D) showing labeling for v-myc in representative immortalized human mesencephalon cells after growth in the proliferative growth condition (FIGS. 2A and 2B) or after differentiation (FIGS. 2C and 2D) for 6 days. For each field, a phase contrast photograph (post-fixation) is shown to the left of the corresponding immunofluorescence photograph.

Differentiation of cell lines with tetracycline resulted in increased neuronal differentiation (FIG. 1) as well as suppression of v-myc oncoprotein expression (FIGS. 2A–2D). An increase in TH expression was also observed for some cell lines, indicating the presence of dopaminergic neurons.

Clonal cell lines were isolated by limit dilution in 96-well plates. Single colonies were expanded by feeding and passaging them as described above. Of eighteen cultures expanded, fourteen appear to be derived from a single cell.

One clone (MESII(1)-C2) was differentiated in DMEM/F-12 with N2 supplement, tetracycline (1 µg/mL), forskolin (10 µM), GDNF (20 ng/mL) and BDNF (20 ng/mL). Following differentiation, a high number of MAP2ab and TH immunoreactive cells were observed. For such immunocytochemistry, cells were fixed with 4% paraformaldehyde, and were incubated with primary antibody in blocking buffer for 2 hours at room temperature, rinsed, and then incubated with a fluorescein (FITC)- or Texas red-conjugated species-specific secondary antibody (Jackson lmmunoresearch Laboratories, Inc., West Grove, Pa.) in blocking buffer for another hour at room temperature. Cultures were then rinsed three times with PBS and coverslipped with PVA/DABCO before scoring and photographing representative fields.

Figure 3:
FIG. 3 is a photograph showing immunofluorescence labeling for tyrosine hydroxylase (TH) in a representative immortalized human mesencephalon cell line after 6 days of differentiation. The culture was differentiated with DMEM/F12 medium containing N2 supplements, tetracycline (1 µg/mL), forskolin (10 µM), BDNF (20 ng/mL), GDNF (20 ng/mL), CNTF (20 ng/mL) and IGF-I (100 ng/mL).

Clone MESII(1)-C2 was also differentiated as described above, but with the addition of CNTF (20 ng/mL) and IGF-I (100 ng/mL). Approximately 11% of the differentiated cells were MAP2ab immunoreactive and 5% of the cells were TH immunoreactive (FIG. 3). In these differentiation conditions, 41% of the MAP2ab positive cells were also TH positive and 100% of the TH positive cells were also MAP2ab positive.

Figure 4:
FIG. 4 is a photograph showing immunofluorescence labeling for GABA in a representative immortalized human mesencephalon cell line after 6 days of differentiation. The culture was differentiated with DMEM/F12 medium containing N2 supplements, tetracycline (1 µg/mL), forskolin (10 µM), BDNF (20 ng/mL), GDNF (20 ng/mL), CNTF (20 ng/mL) and IGF-I (100 ng/mL).

These results indicate that these immortalized human mesencephalon cell lines differentiate into dopaminergic neurons. In addition, other immortalized human mesencephalon cell lines differentiate into GABA-ergic neurons (FIG. 4).

From the foregoing, it will be appreciated that, although specific embodiments of the invention have been described herein for the purpose of illustration, various modifications may be made without deviating from the spirit and scope of the invention. Accordingly, the invention is not limited except by the appended claims.

What is claimed is:

1. A method for producing a conditionally-immortalized human mesencephalon neural progenitor cell, comprising:

(a) plating human mesencephalon cells on a first surface and in first growth medium that permits proliferation;

(b) transfecting said progenitor cells with DNA encoding a selectable marker and an externally regulatable growth-promoting protein; and (c) selecting an adherent monolayer of the transfected cells on a second surface and in a second serum-free growth medium that permits attachment and proliferation, wherein the second serum-free growth medium comprises FGF-2, EGF and PDGF, and therefrom producing a conditionally immortalized human mesencephalon cells in which the growth-promoting protein is regulated by an external factor, such that suppression of the growth promoting protein results in differentiation of the cell into a neuron in the presence of differentiating agents comprising forskolin, GDNF, CNTF, IGF-1 and BDNF.

2. The method of claim 1 wherein the first and second surfaces are independently selected from the group consisting of substrates comprising one or more of a polyamino acid, fibronectin, laminin or tissue culture plastic.

3. The method of claim 1 wherein the growth-promoting gene is an oncogene.

4. The method of claim 3 wherein the oncogene is v-myc.

5. The method of claim 1 wherein expression of the growth-promoting gene is inhibited by tetracycline.

6. A conditionally-immortalized human mesencephalon neural progenitor cell capable of differentiation into neurons in the presence of differentiating agents comprising forskolin, GDNF, CNTF, IGF-1 and BDNF, wherein the cell is transfected with DNA encoding a growth-promoting protein that is regulated by an external factor, such that suppression of the growth-promoting protein results in differentiation of the cell into a neuron, and wherein the cell is polygonal and grows as an adherent monolayer.

7. A conditionally-immortalized human mesencephalon neural precursor cell according to claim 6, wherein the cell is capable of differentiation into dopaminergic neurons.

8. A conditionally-immortalized human mesencephalon neural precursor cell according to claim 6, wherein the cell is capable of differentiation into GABA-ergic neurons.

9. A method for producing a neuron, comprising culturing a cell produced according to claim 1 in the presence of at least one differentiating agent under conditions that inhibit expression of the growth-promoting gene.

10. A method according to claim 9, wherein the cell is cultured in medium comprising tetracycline.

11. A neuron produced according to the method of claim 9.

12. A dopaminergic neuron produced according to the method of claim 9.

13. A GABA-ergic neuron produced according to the method of claim 9.

14. A conditionally-immortalized human mesencephalon neural precursor cell produced according to the method of claim 1.

15. A cell according to claim 14, wherein the cell is present within a clonal cell line.

16. The method of claim 9, wherein the differentiating agent comprises the combination of forskolin, GDNF and CNTF.

17. The method of claim 9 wherein said differentiating agent comprises GDNF.

* * * * *